(12) United States Patent
Iwase

(10) Patent No.: US 9,585,560 B2
(45) Date of Patent: Mar. 7, 2017

(54) IMAGE PROCESSING APPARATUS, IMAGE PROCESSING METHOD, AND PROGRAM

(71) Applicant: CANON KABUSHIKI KAISHA, Tokyo (JP)

(72) Inventor: Yoshihiko Iwase, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 70 days.

(21) Appl. No.: 14/742,293

(22) Filed: Jun. 17, 2015

(65) Prior Publication Data

US 2015/0366452 A1    Dec. 24, 2015

(30) Foreign Application Priority Data

Jun. 18, 2014    (JP) .................. 2014-125729

(51) Int. Cl.
| | | |
|---|---|---|
| A61B 3/14 | (2006.01) | |
| A61B 3/12 | (2006.01) | |
| A61B 3/10 | (2006.01) | |
| A61B 3/00 | (2006.01) | |
| G06T 7/00 | (2006.01) | |

(52) U.S. Cl.
CPC .......... *A61B 3/1233* (2013.01); *A61B 3/0025* (2013.01); *A61B 3/0058* (2013.01); *A61B 3/102* (2013.01); *G06T 7/0012* (2013.01); *G06T 2207/10101* (2013.01); *G06T 2207/30041* (2013.01)

(58) Field of Classification Search
CPC .............. A61B 3/102; A61B 3/14; A61B 3/10
USPC ......... 351/206, 246, 205, 221; 382/128, 131
See application file for complete search history.

(56) References Cited

U.S. PATENT DOCUMENTS

| | | |
|---|---|---|
| 2010/0220914 A1 | 9/2010 | Iwase |
| 2013/0188135 A1 | 7/2013 | Iwase |
| 2013/0194543 A1 | 8/2013 | Iwase |
| 2013/0195340 A1 | 8/2013 | Iwase |
| 2016/0206190 A1* | 7/2016 | Reisman ............... A61B 3/0025 |

FOREIGN PATENT DOCUMENTS

| | | |
|---|---|---|
| CN | 103211574 A | 7/2013 |
| CN | 103315702 A | 9/2013 |
| JP | 2012148141 A | 8/2012 |
| JP | 2013-48696 A | 3/2013 |
| JP | 2013-153884 A | 8/2013 |

* cited by examiner

*Primary Examiner* — Hung Dang
(74) *Attorney, Agent, or Firm* — Canon U.S.A., Inc. IP Division

(57) ABSTRACT

An image processing apparatus includes an information acquiring unit configured to acquire information indicating a shape of a plurality of regions in at least one layer in a tomographic image including a plurality of layers in an eye fundus of an eye to be examined and a determination unit configured to determine whether an anomaly is present in the plurality of regions based on the information indicating the shape.

20 Claims, 13 Drawing Sheets

| | SHAPE | SIGN | CURVATURE MAGNITUDE |
|---|---|---|---|
| R1 | | NEGATIVE | SMALL |
| R2 | | POSITIVE | SMALL |
| R3 | | ZERO | ZERO |
| R4 | | POSITIVE | LARGE |
| R5 | | NEGATIVE | LARGE |

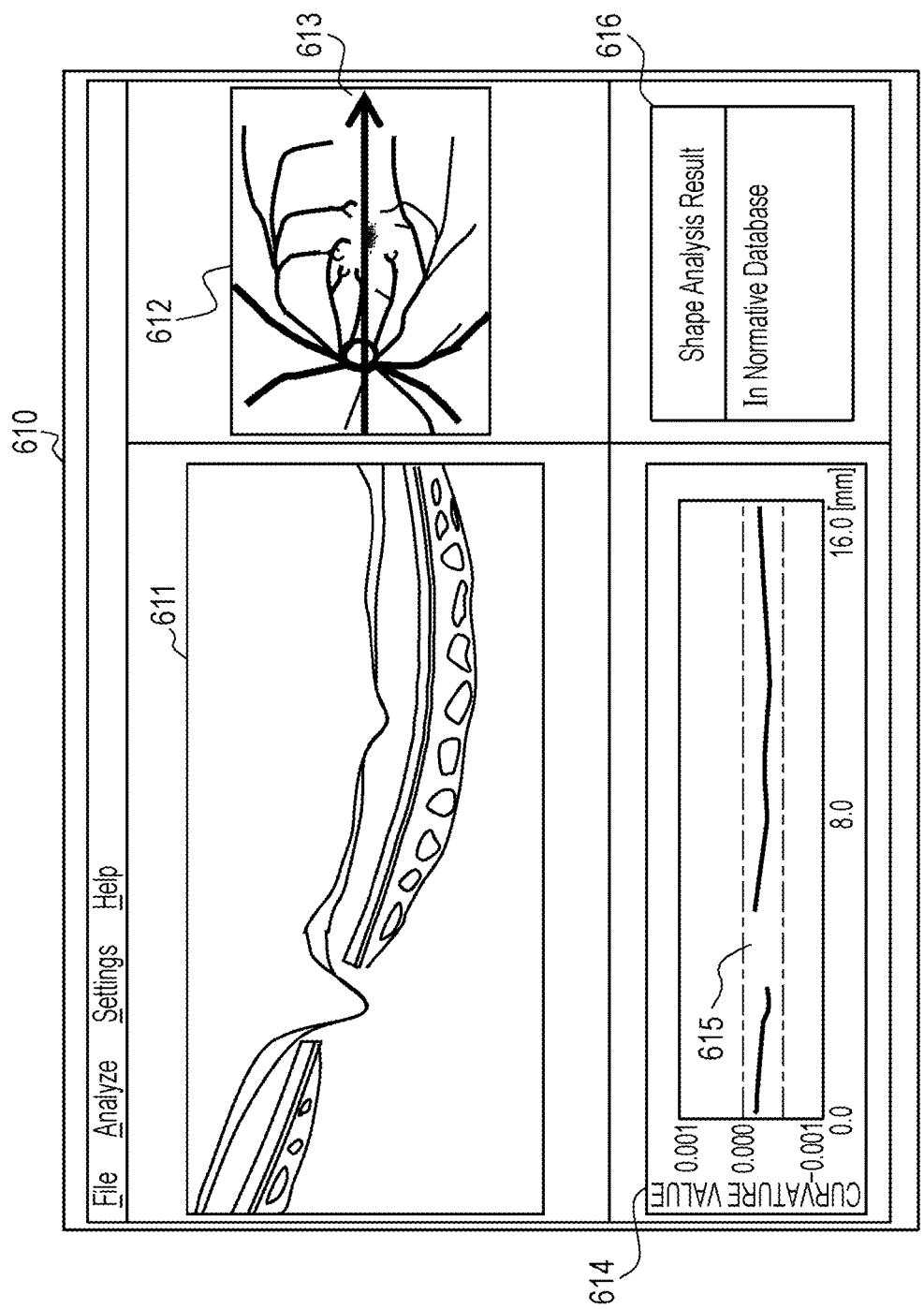

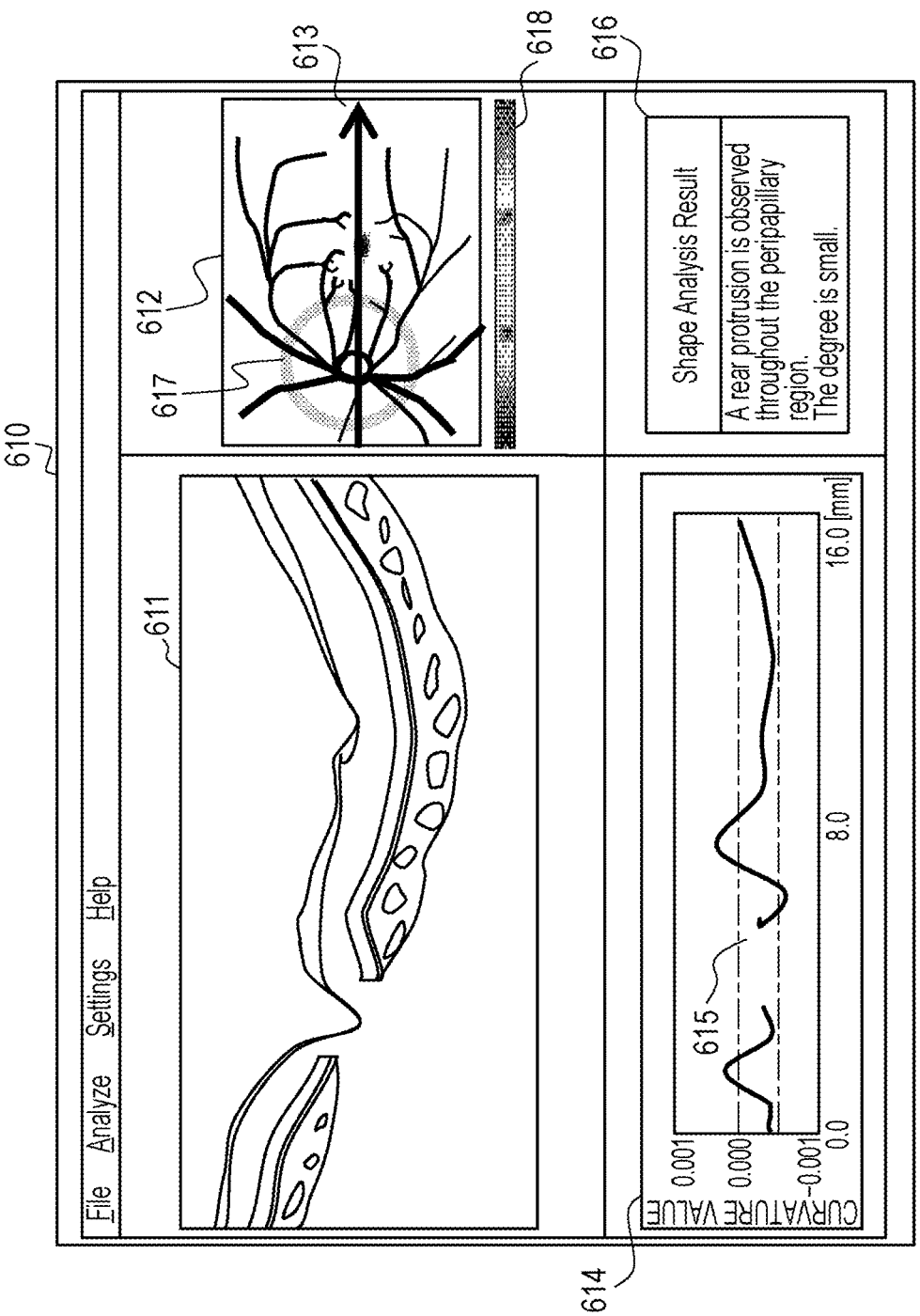

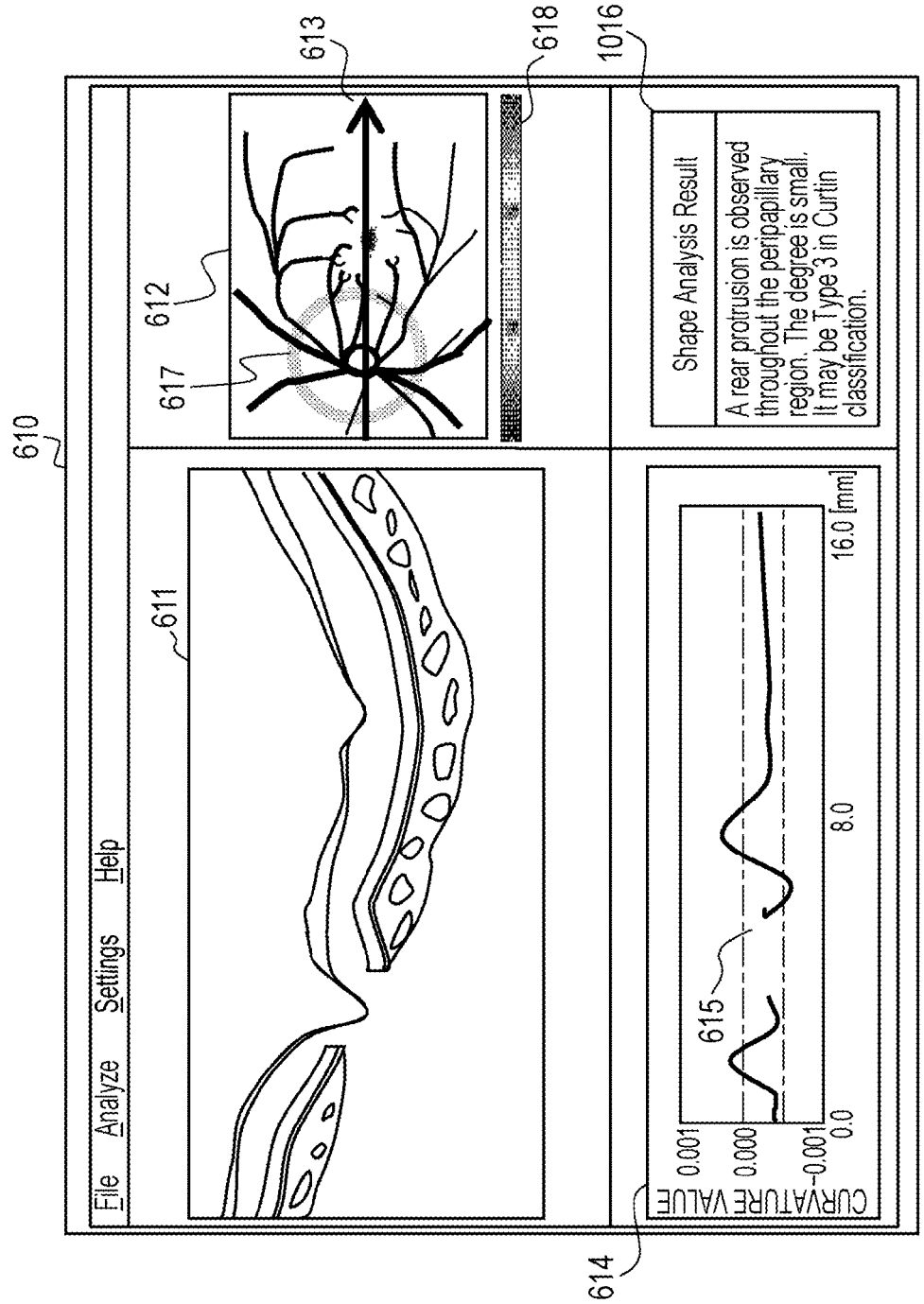

FIG. 10B

| DEGREE | VALUE |
|---|---|
| LARGE | Th2 < Value |
| MEDIUM | Th1 ≤ Value ≤ Th2 |
| SMALL | Value < Th1 |

FIG. 10C 1016-1

| SHAPE ANALYSIS RESULT |
|---|
| Curtin Classification<br>Type3: Probability ○ %<br>Type4: Probability △ % |

IMAGE PROCESSING APPARATUS, IMAGE PROCESSING METHOD, AND PROGRAM

BACKGROUND OF THE INVENTION

Field of the Invention

The present invention relates to an image processing apparatus for processing an image of an object to be examined, an image processing method, and a program.

Description of the Related Art

A tomographic imaging apparatus for eye portions, such as an optical coherence tomographic imaging apparatus (referred to as OCT), can observe a state of the inside of a retina layer three-dimensionally. The tomographic imaging apparatus is useful in more accurately diagnosing diseases, and it has received attention in recent years. One example of OCT is time domain OCT (TD-OCT) using a combination of a light source having a board-band region and a Michelson interferometer. With this, information on the strength of a signal with respect to a position in a depth direction is obtainable by detecting interferential light of reference light and backward scattered light from an object to be examined, the object to which measurement light has been emitted in a measurement optical path, while moving a reference mirror in a reference optical path along the optical axis direction.

Because the interferential light is measured while the reference mirror is mechanically moved, it is difficult for the TD-OCT to obtain a tomographic image at high speeds. One known method for obtaining a tomographic image at higher speeds is spectral domain OCT (SD-OCT) as OCT that obtains an interferogram by a spectroscope using a broadband light source. Another known example is swept source OCT (SS-OCT) employing the technique of measuring spectrum coherence by a single-channel photo detector by using a high-speed wavelength-sweeping light source.

There is high myopia in which degeneration of tissue at an ocular posterior pole increases the eye's axial length and it causes symptoms of a high degree of myopia. Traditionally, a doctor subjectively evaluates the shape of the ocular posterior pole to determine whether an eye to be examined has high myopia or not by using a tomographic image, a picture of the eye fundus. Thus the determination varies depending on the evaluator. An image processing apparatus for quantitatively measuring the shape of the ocular posterior pole (the degree of a curve of the retina) to reduce the variations in the determination is disclosed in Japanese Patent Laid-Open No. 2013-153884. Japanese Patent Laid-Open No. 2013-153884 discloses determination of whether an eye to be examined has symptoms of posterior staphyloma by comparison with a normal range in a statistical database in a biaxial map of a mean value of a curvature and a variance of the curvature.

Japanese Patent Laid-Open No. 2013-48696 discloses an image analysis apparatus for ophthalmological diseases. This image analysis apparatus automates and quantifies the analysis to minimize determination dependent on a subject of a radiologist in diagnosis using 3D voxel MRI images of a head portion, including an eyeball. It discloses a quantification by calculating the eye's axial length and the degree of asymmetry with respect to the eye axis as parameters for image analysis. It also discloses classification of the high myopia types based on the MRI.

SUMMARY OF THE INVENTION

An image processing apparatus according to an aspect of the present invention includes an image obtaining unit configured to obtain a tomographic image including a plurality of layers in an eye fundus of an eye to be examined;

an information acquiring unit configured to acquire information indicating a shape of a macula portion and an optic disk portion in at least one layer in the tomographic image; and a determination unit configured to determine whether an anomaly is present in the macula portion and the optic disk portion based on the information indicating the shape.

Further features of the present invention will become apparent from the following description of exemplary embodiments with reference to the attached drawings.

BRIEF DESCRIPTION OF THE DRAWINGS

FIGS. 6A and 6B illustrate examples of displaying analysis results on a display area in a display portion in the image processing system according to the first embodiment.

FIGS. 10A to 10C illustrate example analysis results on the display area in the display portion in the image processing system according to the second embodiment.

DESCRIPTION OF THE EMBODIMENTS

Figure 1:
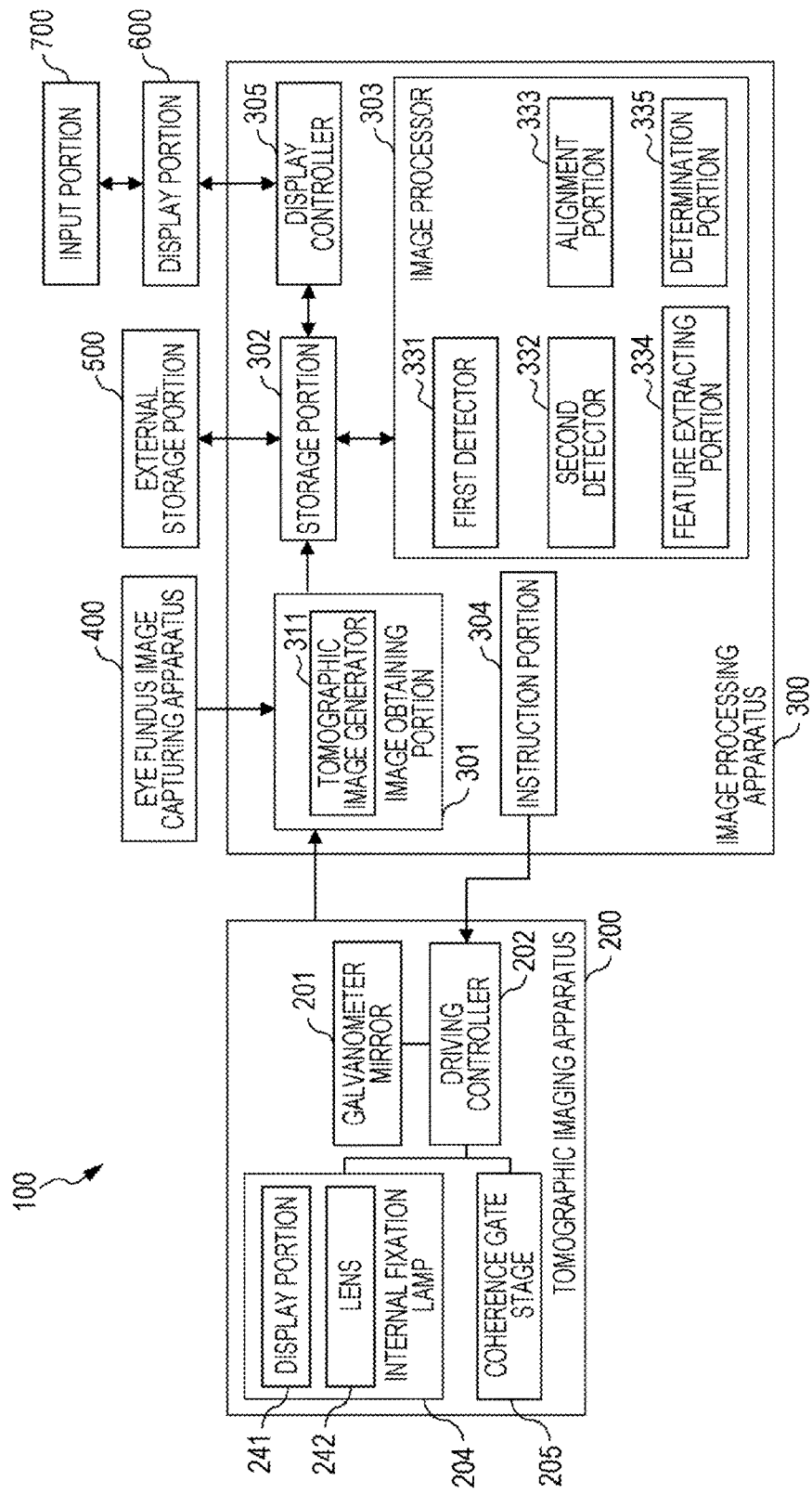
FIG. 1 illustrates a configuration of an image processing system according to a first embodiment.

Typically, a general shape of an eyeball can be observed by using MRI images. Because the MRI images are in relatively low spatial resolution, it is difficult to minutely observe the shape of the eye fundus. If an anomaly is present in the eye fundus, doctors have to know very minutely the region where it is present to carry out diagnosis and treatment accurately. Unfortunately, however, it is difficult for the doctors to objectively identify a region where the anomaly is present in the eye fundus without subjective variability when the shape of the eye fundus is abnormal.

The present invention can provide an image processing apparatus that can enable a doctor to easily identify a region where an anomaly is present in an eye fundus when the eye fundus has an abnormal shape, an image processing method, and a program.

According to an aspect of the present invention, whether an anomaly is present in a plurality of regions can be determined based on information indicating the shape of the plurality of regions in at least one layer in a tomographic image. Examples of the plurality of regions may be a region corresponding to the macula portion and a region corresponding to the optic disk portion in the layer. One example of the information indicating the shape may be curvatures of the plurality of regions in the layer in the tomographic image of the eye fundus. The region where the presence of the anomaly is determined can be displayed on the display unit in a state where it is superimposed on an eye fundus image of the eye to be examined, for example. The type corresponding to the region where the presence of the anomaly is determined and the type corresponding to the region where the presence of the anomaly is determined and corresponding to a state of that anomaly (e.g., Curtin classification) can be determined. Accordingly, an image processing apparatus that can enable a doctor to easily identify a region where an anomaly is present in an eye fundus when the eye fundus has an abnormal shape, an image processing method, and a program can be provided.

According to another aspect of the present invention, at least one type of a plurality of types (e.g., Curtin classification) corresponding to a region where an anomaly is present in an eye fundus can be determined based on information indicating a shape of at least one layer in a tomographic image. The determined type can be displayed on the display unit, for example. Accordingly, an image processing apparatus that can enable a doctor to easily identify a region where an anomaly is present in an eye fundus when the eye fundus has an abnormal shape, an image processing method, and a program can be provided.

Embodiments of the present invention will be described below with reference to the drawings.

First Embodiment

Quantitative Measurement of Local Shape of Eye Fundus

An image processing system including an image processing apparatus according to the first embodiment can quantitatively measure a local shape of an eye fundus. The image processing system including the image processing apparatus according to the first embodiment is described below with reference to the drawings.

(Image Processing System Including Image Processing Apparatus)

FIG. 1 illustrates a configuration of an image processing system 100 including an image processing apparatus 300 according to the present embodiment. As illustrated in FIG. 1, the image processing system 100 is configured such that the image processing apparatus 300 is connected to a tomographic imaging apparatus (also referred to as OCT) 200, an eye fundus image capturing apparatus 400, an external storage portion 500, a display portion 600, and an input portion 700 through interfaces.

The tomographic imaging apparatus 200 is an apparatus that captures a tomographic image of an eye portion. Examples of an apparatus used as the tomographic imaging apparatus may include an SD-OCT or SS-OCT. The tomographic imaging apparatus 200 is a known apparatus, and its detailed description is omitted. Here, an imaging range for a tomographic image and setting of a parameter in an internal fixation lamp 204 set by an instruction from the image processing apparatus 300 are described here.

In FIG. 1, a galvanometer mirror 201 is used to scan an eye fundus by using measurement light and defines the imaging range for the eye fundus in OCT. A driving controller 202 defines the imaging range and the number of scanning wires in a plane direction (scanning rate in the plane direction) in the eye fundus by controlling the driving range and velocity of the galvanometer mirror 201. Here, for the sake of the simplification, the galvanometer mirror is illustrated as a single mirror, but in actuality, it includes two mirrors consisting of a mirror for X scan and a mirror for Y scan. The galvanometer mirror 201 can enable scanning a desired range in the eye fundus by using measurement light.

The internal fixation lamp 204 includes a display portion 241 and a lens 242. As the display portion 241, a matrix arrangement of a plurality of light emitting diodes (LD) is used. The lighting position of each light emitting diode is changed under control by the driving controller 202 in accordance with a region where an image is to be captured. Light from the display portion 241 is guided to an eye to be examined through the lens 242. The light emitted from the display portion 241 has a wavelength of 520 nm. A desired pattern is displayed by the driving controller 202.

Figure 3A:
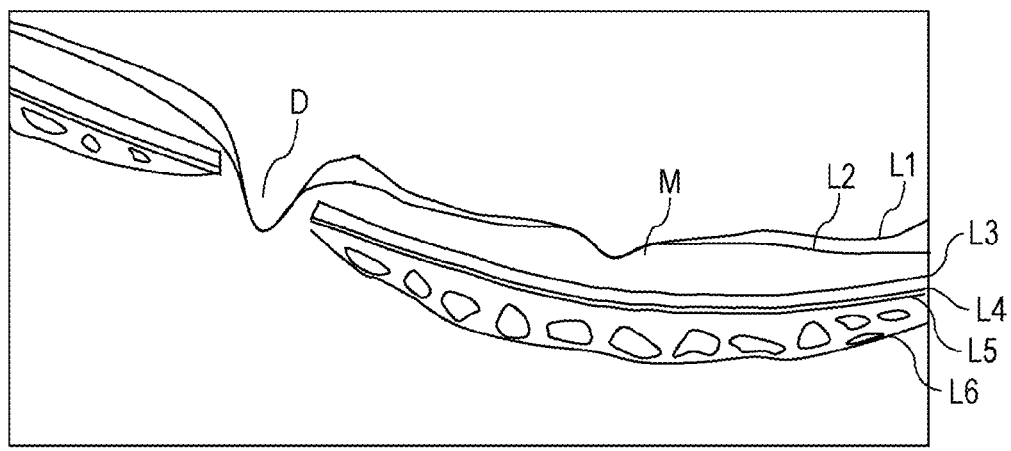
FIGS. 3A and 3B are illustrations for describing a tomographic image of an eye portion and an image of an eye fundus obtained by an image processing apparatus according to the first embodiment.

A coherence gate stage 205 is controlled by the driving controller 202 to support differences of the eye's axial length of the eye to be examined and the like. The coherence gate indicates a position where measurement light and reference light have the same optical distance in OCT. By controlling the coherence gate, whether the position of the coherence gate is on a retina layer side or on a side deeper than the retina layer can be determined. One example of the image capturing method used in the present embodiment is an enhanced depth imaging (hereinafter referred to as EDI) method. When images are captured by this EDI method, the position of the coherence gate is set on the side deeper than the retina layer. Thus, the EDI method has characteristics of enabling images of a choroid and a retinal pigment epithelium layer to be captured with high intensity. FIG. 3A illustrates a tomographic image of an eye portion. In FIG. 3A, L1 indicates the boundary between an inner limiting membrane (ILM) and a nerve fiber layer (NFL), L2 indicates the boundary between the NFL and a ganglion cell layer (GCL), L3 indicates a joint (junction) between an inner photoreceptor segment and an outer photoreceptor segment (ISOS), L4 indicates a retinal pigment epithelium (RPE) layer, L5 indicates a Bruch's membrane (BM), and L6 indicates a choroid. M indicates a macula portion (central portion of the macula indicates a fovea centralis), and D indicates an optic disk portion.

Figure 3B:
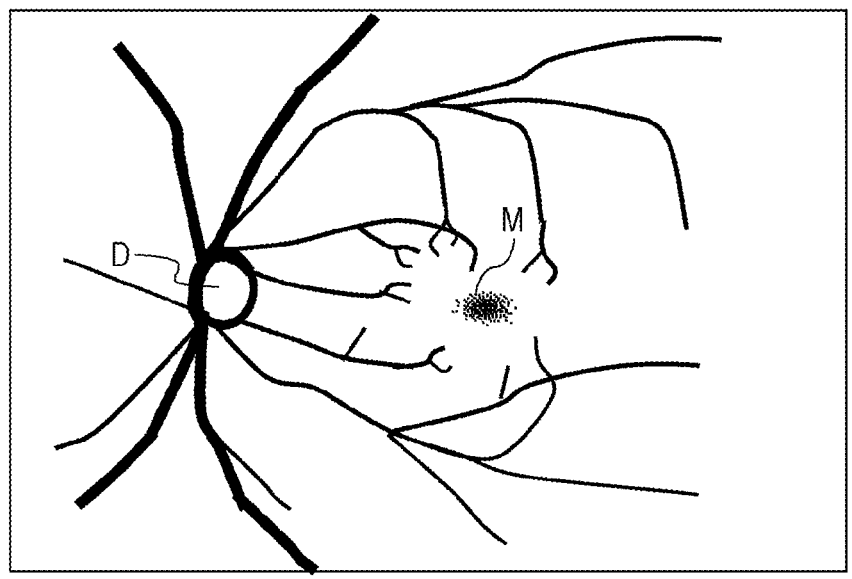

The eye fundus image capturing apparatus 400 is an apparatus for capturing an eye fundus image of an eye portion. Examples of the eye fundus image capturing apparatus 400 may include an eye fundus camera and a scanning laser ophthalmoscope (SLO). FIG. 3B illustrates an eye fundus image of an eye portion. In FIG. 3B, M indicates the macula portion, and D indicates the optic disk portion.

The image processing apparatus 300 includes an image obtaining portion 301, a storage portion 302, an image processor 303, an instruction portion 304, and a display controller 305. The image obtaining portion 301 includes a tomographic image generator 311 and is configured to obtain signal data of a tomographic image captured by the tomographic imaging apparatus 200, perform signal processing, and thus generate the tomographic image. The generated tomographic image is stored in the storage portion 302. The image processor 303 includes a first detector 331, a second detector 332, an alignment portion 333, a feature extracting portion 334, and a determination portion 335. The first detector 331 is configured to detect a retina layer from the tomographic image. The second detector 332 is configured to detect feature regions, including a macula portion and a papilla portion, of the retina from the tomographic image or eye fundus image. The alignment portion 333 is configured to perform alignment between a plurality of tomographic images or alignment between a tomographic image and an eye fundus image. The feature extracting portion 334 is configured to extract shape features of the retina layer detected by the first detector 331. The determination portion 335 is configured to perform determination based on the quantity of the features extracted by the feature extracting portion 334. The instruction portion 304 is configured to provide the tomographic imaging apparatus 200 with an instruction about, for example, an imaging parameter for use in capturing an image of a desired retina layer region.

The external storage portion 500 retains information about an eye to be examined (e.g., name, age, and gender of a patient) and each of captured image data, an imaging parameter, an image analysis parameter, and a parameter set by an operator in association with each other.

Examples of the input portion 700 may include a mouse, keyboard, and a touch screen. The operator can provide instructions to the image processing apparatus 300, tomographic imaging apparatus 200, and eye fundus image capturing apparatus 400 by using the input portion 700.

(Operation Process in Image Processing System)

Figure 2:
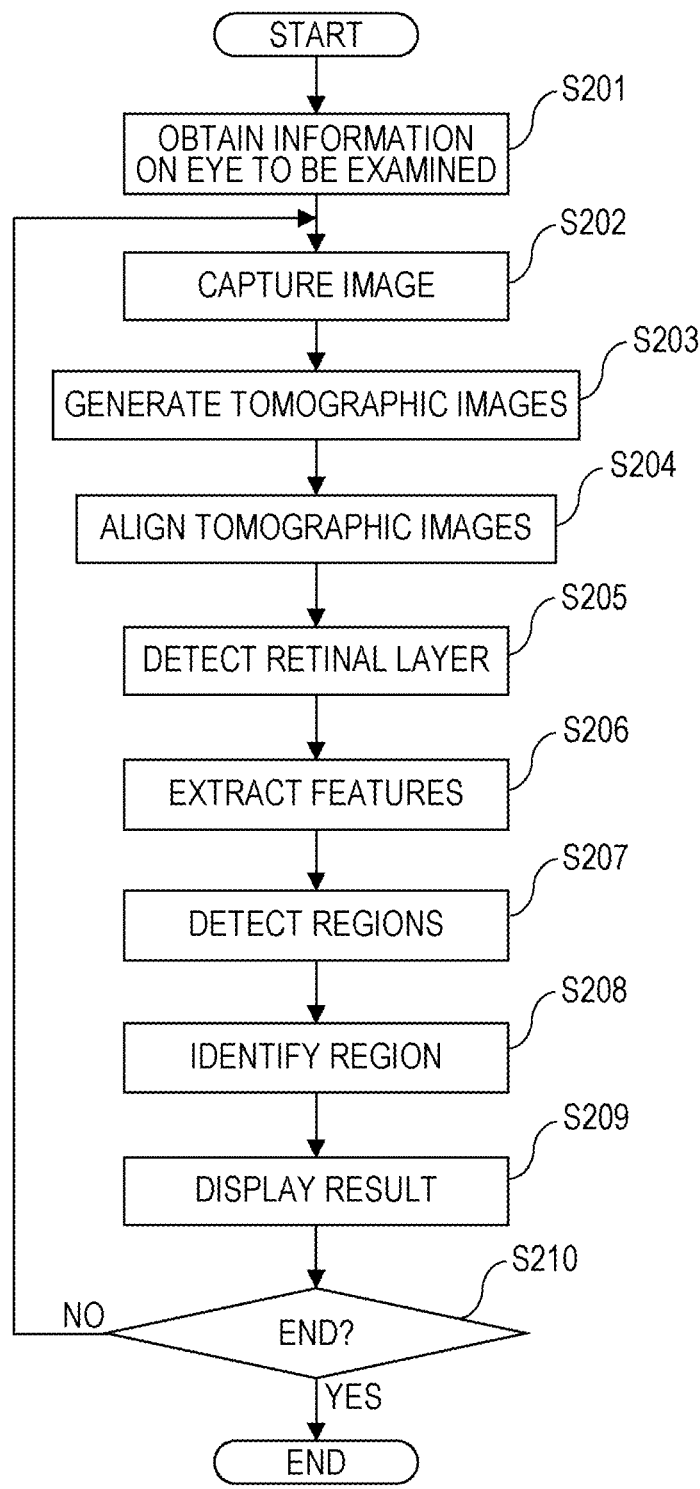
FIG. 2 is a flowchart that illustrates an operation process in the image processing system according to the first embodiment.

Next, a processing procedure in the image processing system 100 according to the present embodiment is described with reference to FIG. 2. FIG. 2 is a flowchart that illustrates an operation process in the image processing system 100 according to the present embodiment. The operation process in the image processing apparatus 300 according to the present embodiment starts at step S203.

<Step S201: Acquisition of Information on Eye to be Examined>

At step S201, a unit configured to acquire information on an eye to be examined (not illustrated) acquires an identification number of a test subject as information for identifying the eye to be examined, from the outside. It acquires information about the eye to be examined retained in the external storage portion 500 based on the identification number of the test subject and stores it in the storage portion 302.

<Step S202: Capturing of Images of Eye to be Examined>

At step S202, the tomographic imaging apparatus 200 captures an image of the eye to be examined. First, it adjusts various imaging parameters to capture the image. Specifically, it sets at least the position of the internal fixation lamp, the scanning range, the scanning pattern, and the position of the coherence gate. The driving controller 202 controls the light emitting diodes in the display portion 241 and controls the position of the internal fixation lamp 204 to capture images of the center of the macula portion and the optic disk.

In the present embodiment, the imaging mode in image capturing can be selected, and a case where images are captured in retina layer shape analysis imaging mode is discussed. This imaging mode name is merely an example, and the imaging mode is not limited to that. The imaging mode is the one in which the scanning pattern, the position of the internal fixation lamp, and the analysis method are set in combination in advance, and a frequently used mode, such as imaging mode for glaucoma, may be set. In the retina layer shape analysis imaging mode in the present embodiment, the scanning range is set to the range of 10 to 20 mm. This numerical value is an example, may vary in accordance with the specifications of the apparatus, and may preferably be set to a range that contains both the macula portion and the papilla portion. The scanning pattern is set to the one covering the entire retina layer in raster scanning or radial scanning in which three-dimensional volume images can be captured. The position of the coherence gate is described as the one when images are captured on the vitreous body side.

After imaging preparation, imaging is performed. To capture images of an eye to be examined, when an operator selects an imaging instruction button (not illustrated), the tomographic imaging apparatus 200 controls the driving controller 202, activates the galvanometer mirror 201, and captures tomographic images. The galvanometer mirror 201 includes an X scanner for the horizontal direction and a Y scanner for the vertical direction. When the directions of these scanners are changed individually, scanning can be made in each of the horizontal direction (X) and the vertical direction (Y) in the apparatus coordinate system. When the directions of these scanners are changed at the same time, scanning can be made in a direction in which the horizontal and vertical directions are combined. Thus, scanning can be made in any direction on an eye fundus plane.

<Step S203: Generation of Tomographic Images>

At step S203, the tomographic image generator 311 generates tomographic images. When the tomographic imaging apparatus is an SS-OCT, for example, the tomographic image generator 311 generates tomographic images by performing typical reconstruction processing on interfering signals output from difference detectors (not illustrated).

First, the tomographic image generator 311 reduces fixed pattern noise in interfering signals. The fixed pattern noise is reduced by leveling a plurality of detected A scan signals, extracting fixed pattern noise, and subtracting it from input interfering signals. Next, the tomographic image generator 311 performs desired window function processing to optimize depth resolution and dynamic range that are in trade-off relation when they are subjected to the Fourier transform in a finite interval. Then, tomographic signals are produced by the FFT processing.

The image processing apparatus according to the present invention may be connected to a tomographic imaging apparatus, for example, such that they can communicate with each other. When it obtains tomographic images generated in the tomographic imaging apparatus, image obtaining portion 301 may execute this step as obtaining tomographic images.

<Step S204: Alignment of Tomographic Images>

At step S204, the alignment portion 333 aligns the plurality of tomographic images generated at step S203. In the present embodiment, a case where images are captured by raster scanning in which three-dimensional volume images can be captured is discussed. One example of the alignment is described below. An evaluation function indicating the similarity between two tomographic images is defined in advance, and the tomographic images are deformed such that the value of this evaluation function is optimized. One example of the evaluation function may be the one obtained by an evaluation method using a pixel value (one example of such an evaluation method may be the one using a correlation coefficient).

An expression applied when the correlation coefficient is used as the evaluation function indicating the similarity is given as Expression 1-1 below.

$$\frac{\left(\iint_S (f(x,y) - \bar{f})(g(x,y) - \bar{g}) dx dy\right)}{\left(\sqrt{\iint_S (f(x,y) - \bar{f})^2 dx dy \iint_S (g(x,y) - \bar{g})^2 dx dy}\right)} \quad \text{Expression 1-1}$$

In Expression 1-1, a region of the first tomographic image is f(x, y), and a region of the second tomographic image is g(x, y). Here, in Expression 1-1, the mean of the region f(x, y) and the mean of the region g(x, y) are provided in Expressions 1-2 and 1-3 below.

$$\bar{f} \quad \text{Expression 1-2}$$

$$\bar{g} \quad \text{Expression 1-3}$$

The region used here is a pixel region for use in alignment, typically it is set to a region equal to or smaller than the size of a tomographic image, and it may preferably be set to the one including the retina layer region in the case of a tomographic image for an eye. Examples of the processing of deforming images may include translation or rotation using affine transformation and changing the enlargement factor.

The alignment may be performed on a feature point basis. For example, features of, for example, a retina layer and lesion are extracted from a two-dimensional tomographic image. The alignment can be performed by selecting stably detected feature points by using the extraction results.

If the tomographic imaging apparatus has the function of tracking the eye fundus, positional deviation in a plurality of tomographic images caused by motion of the eye to be examined is relatively small. If the fixation of the eye to be examined is stable, positional deviation in a plurality of tomographic images is also relatively small. In these cases, this step may be omitted in the operation process in the image processing apparatus according to the present invention.

<Step S205: Detection of Layer from Tomographic Image>

At step S205, the first detector 331, which is one example of a layer detecting unit, detects a boundary in the retina layer from a tomographic image (performs segmentation). The first detector 331 can detect any one of the boundaries of L1 to L6 in the tomographic image illustrated in FIG. 3A. Images are generated by applying a median filter and a Sobel filter on a tomographic image that is a target for processing (hereinafter referred to as median image and Sobel image). Profiles are generated for each A scan from the generated median image and Sobel image. The profile from the median image is an intensity value, whereas the profile from the Sobel image is a gradient. Then, a peak is detected from the profile generated from the Sobel image. The profiles from the median images corresponding to before and after the detected peak or between the peaks are referred to, and the boundaries in the retina layer in the regions are detected.

The image processing apparatus capable of automatically detecting layer boundaries from a tomographic image according to the present embodiment, as described above, is convenient for users. However, the image processing apparatus may be configured such that a user can specify a layer manually or such that an automatically detected layer can be corrected manually. If the user can specify a layer manually, this step may be omitted in the operation process in the image processing apparatus according to the present embodiment.

<Step S206: Acquisition of Information Indicating Shape>

At step S206, a case is discussed where the feature extracting portion 334, which is an example of an information acquiring unit, measures curvatures in a plurality of regions in a retina layer (e.g., regions corresponding to the optic disk portion and the macula portion in the layer) as features of the shape of the retina layer, which are examples of information indicating the shape. The description is provided using the tomographic image illustrated in FIG. 3A. In FIG. 3A, the axis of abscissa is the x coordinate, the axis of ordinate is the z coordinate, and the curvature of a boundary line in a layer being a target for shape analysis is calculated. In the present embodiment, the layer being a target for shape analysis in evaluation of the shape of an ocular posterior pole may preferably be a Bruch's membrane (also called Bruch layer). This is because it is known that the Bruch's membrane is insensitive to a lesion, such as age-related macular degeneration, from an anatomical point of view. Typically, a layer deeper than a layer where a lesion exists is considered to be insensitive to the lesion, and thus the RPE layer, which is a relatively deep position, may also be preferable.

The curvature κ can be obtained by calculating Expression 2 at each point in the boundary line (position of each A scan). In Expression 2, to have a local shape change, one example range used in calculation of the curvature is the one using the points at both sides 500 µm away from the reference point as the center. That is, it corresponds to approximating the range of 1 mm (1000 µm) whose center is each of the points in the boundary line with a circle.

$$\kappa = \frac{\frac{d^2 z}{dx^2}}{\left(1 + \left(\frac{dz}{dx}\right)\right)^{\frac{3}{2}}} \quad \text{Expression 2}$$

Figure 4:
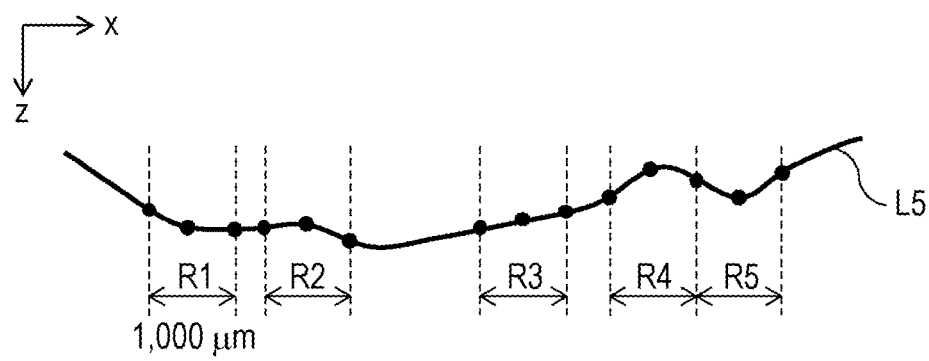
FIG. 4 is an illustration for describing shape analysis in the image processing apparatus according to the first embodiment.

This is described below with reference to FIG. 4. The line in FIG. 4 illustrates a layer boundary line that is a target for shape analysis for the sake of simplification (L5, Bruch's membrane, in the present embodiment). FIG. 4 illustrates an example in which the solid circles on the layer boundary line indicate the places where calculation is performed in Expression 2. The table in FIG. 4 illustrates signs and magnitudes of the curvatures when they are calculated in the positions in R1 to R5. R1 in FIG. 4 indicates a small convex shape to the choroid side. Here, the curvature has a negative sign and a small value. R3 in FIG. 4 indicates a case where three points in the range of 1 mm are aligned linearly and thus the magnitude of the curvature is zero. FIG. 4 illustrates the R1 to R5 regions not overlapping each other. In actuality, the regions for calculation in the positions of A scans overlap each other. In the present embodiment, the calculation range is 1 mm. This value may change in accordance with the size of a structure whose local change is to be observed. That is, to observe a more minute change, the pitch may be narrowed, and to observe a larger change, the pitch may be widened. Because Expression 2 represents the curvature with a sign, the sign of κ indicates an upward convex shape or a downward convex shape, and the magnitude of the numerical value indicates the degree of the curve of the shape. Thus, when the convexity on the vitreous body side is plus and the convexity on the choroid side is minus, in the case where the sign of the curvature is in a minus range, plus range, and minus range in each tomographic image, the shape is a W shape.

The present embodiment illustrates the case where the curvature in a boundary line in a tomographic image is calculated. The calculation of the curvature is not limited to such a case. A three-dimensional curvature may be calculated from three-dimensional data. To support shape changes of various sizes, local shapes may be calculated in multiple scales (e.g., 1 mm, 1.5 mm, and 2 mm ranges).

The information indicating the shape may not be the curvature. It may be a value indicating a region from a layer, such as an RPE, to a reference line in a tomographic image (e.g., area, volume, or distance in a depth direction). This is described below using FIGS. 11A to 11D. FIGS. 11A to 11D are illustrations for describing shape analysis in the image processing apparatus according to the first embodiment. Because the shape of the optic disk portion varies from person to person, a mask region 1101 may preferably be set to the optic disk portion such that the optic disk portion is removed from a target forming the above-described area or volume.

Figure 11A:
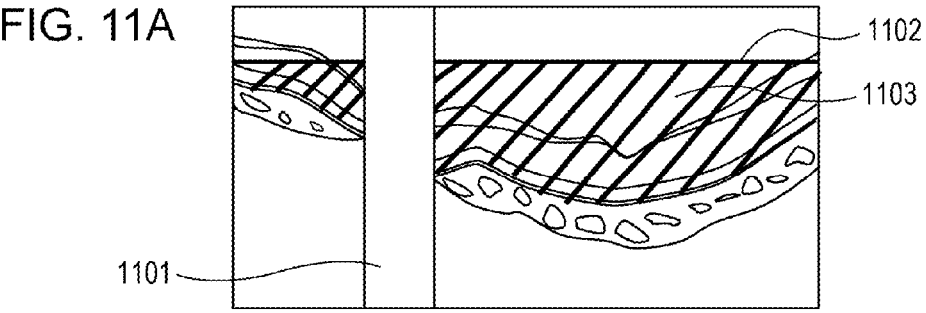
FIGS. 11A to 11D are illustrations for describing shape analysis in the image processing apparatus according to the first embodiment.
Figure 11B:
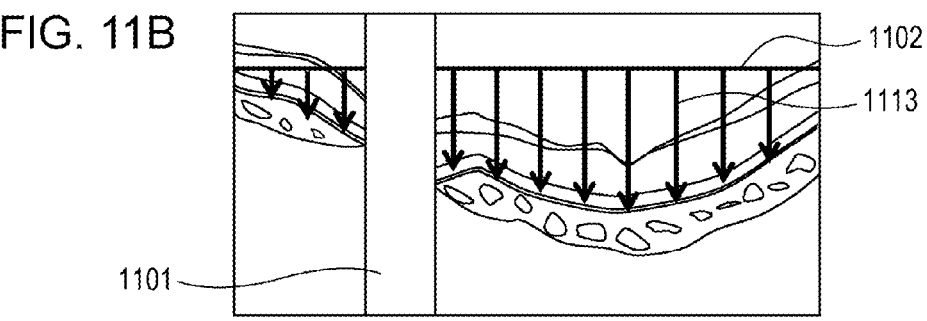

First, in FIGS. 11A and 11B, a reference line 1102 is set at a certain height from the deepest portion of the RPE (e.g., 500 μm depth position or the shallowest position in the RPE). The information indicating the shape may be an area 1103 (volume in a three-dimensional image) of the hatched region from the reference line 1102 to the RPE or a distance 1113 from the reference line 1102 to the RPE.

Figure 11C:
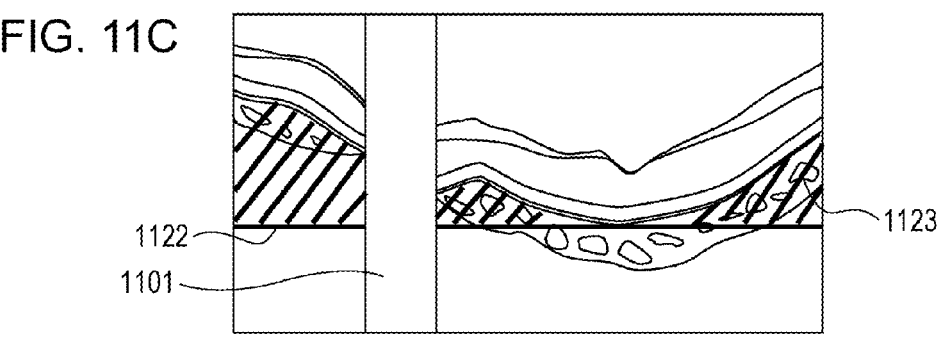
Figure 11D:
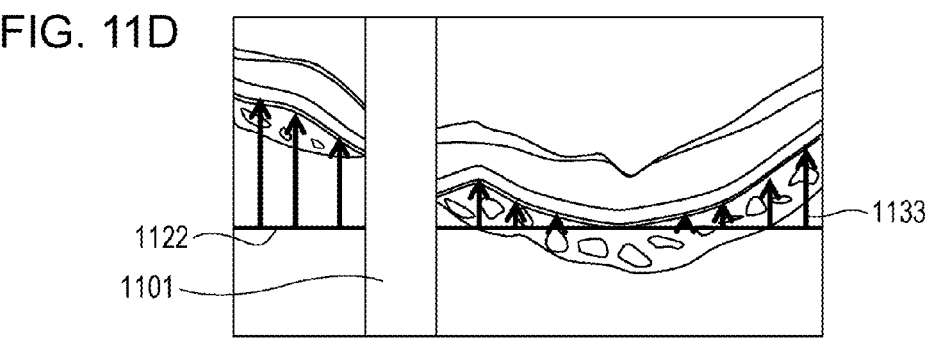

FIGS. 11C and 11D illustrate an example in which the reference line illustrated in FIGS. 11A and 11B is changed in the depth direction and the deepest portion of the RPE is set at a reference line 1122. In this case, the information indicating the shape may be an area 1123 (volume in a three-dimensional image) of the hatched region from the reference line 1122 to the RPE or a distance 1133 from the reference line 1122 to the RPE.

<Step S207: Detection of Plurality of Regions>

At step S207, the second detector 332, which is an example of a region detecting unit, detects the optic disk portion and the macula portion, which are examples of the plurality of regions. First, detection of the optic disk portion from a tomographic image is described.

As illustrated in FIG. 3A, the optic disk portion has a shape feature of the retina layer in which it is recessed to the choroid side and has a boundary line feature of the retina layer in which the boundary lines of the IS/OS and the RPE are absent. By employing these features, the optic disk portion is detected by the use of the layer boundary line result of detection by the first detector 331. If heavy bleeding is present in the retina layer, the intensity value of each of the IS/OS and RPE is low, and thus the boundary line feature of the retina layer is similar to the feature of the optic disk portion at the bleeding point. However, in the case of such bleeding, because the retina layer swells (it has a convex shape to the vitreous body side), the retina layer has a shape feature significantly different from that of the optic disk portion. Thus, the optic disk portion can be detected by employing the shape feature of the retina layer and the boundary line feature inside the retina layer. The method for detecting the optic disk portion is not limited to this method and may be detection using the eye fundus image illustrated in FIG. 3B. For example, the optic disk portion may be detected by using blood vessel features of a blood vessel detected from the eye fundus image. Because the blood vessel has a thin linear structure, the blood vessel is detected by using a filter that enhances the linear structure. An example of the filter enhancing the linear structure may be a differential filter, such as a Sobel filter or a Laplacian filter. Blood vessels spread from the optic disk portion over the eyeball in the eye fundus. Thus, the location where the blood vessels are dense is identified as the optic disk portion. In the present embodiment, the eye fundus image is described as a picture obtained by an SLO (scanning laser ophthalmoscopy) or an eye fundus camera. A pseudo eye fundus image can also be generated by generating an integrated image in which tomographic images are integrated in the depth direction. Thus, the optic disk portion may be detected by detection of a blood vessel from the pseudo eye fundus image as the eye fundus image. The optic disk portion may also be detected by using information about the image capturing. FIGS. 3A and 3B are a tomographic image and a plane image of a left eye. If the images are captured such that the macula portion is centered, the optic disk portion exists in the vicinity of the center on the left side in the display area. Thus the above-described method may be applied after the range where the optic disk portion is assumed to exist may be restricted to a certain degree by using information about the position of the fixation lamp at the time of image capturing and the eye whose images are captured (right or left eye).

Next, detection of the fovea centralis of the macula portion is described. As illustrated in FIG. 3A, in a tomographic image, the macula portion has a shape feature of the retina layer in which it is slightly recessed to the choroid side and has a boundary line feature of the retina layer in which the boundary lines are absent or are integral with the ILM because there is no NFL. By employing these features, the macula portion is detected by the use of the layer boundary line result of detection by the first detector 331. The macula portion may also be detected after the range where it is assumed to exist is restricted to a certain degree based on information about the image capturing and the positional relationship with the optic disk portion, as in the case of the processing described for the optic disk portion. That is, if images are captured such that the center of the macula portion is centered, because the macula portion exists in the vicinity of the center in the display area, the macula portion may be detected after the range is restricted to the vicinity of the center in the display area. When the optic disk portion has been detected, because the ratio (DM/DD ratio) of the distance from the center of the papilla to the fovea centralis of the macula portion (DM) to the diameter of the optic disk (DD) and is typically 2.4 to 3.0, the macula portion may be detected in a region that falls within that range. Because 2.4 to 3.0 are values within a normal range, if the papilla size is large or small, the ratio is outside that ratio range. Thus, the ratio value range may also be set at 2.0 to 3.5.

The image processing apparatus capable of automatically detecting an optic disk portion and a macula portion according to the present embodiment is convenient for users, as described above. The image processing apparatus may also be configured such that a user can specify the regions manually or such that the position of an automatically detected region can be modified manually. If the user can specify a region manually, this step may be omitted in the operation process in the image processing apparatus according to the present embodiment.

<Step S208: Identification of Region where Anomaly is Present in Eye Fundus>

At step S208, the determination portion 335, which is an example of a determination unit, identifies a region where an anomaly is present in an eye fundus by employing the features extracted by the feature extracting portion 334 (curvatures of a plurality of regions in a layer, the curvatures being an example of the information indicating the shape) and the positions of the regions detected by the second detector 332.

The determination portion 335 conducts comparison with a normative database for the quantities of shape features stored in the external storage portion 500. The normative database used here is the one generated from data of many eyes and generated by integrating race-specific data and age-specific data. In the ophthalmological field, the data may be organized by an eye-specific parameter, such as the position of an eye (left/right) or the eye's axial length. Example settings in the normative database may be such that a 95% range of the normal data is normal, a 4% range is the borderline, and the remaining 1% is abnormal.

Figure 5A:
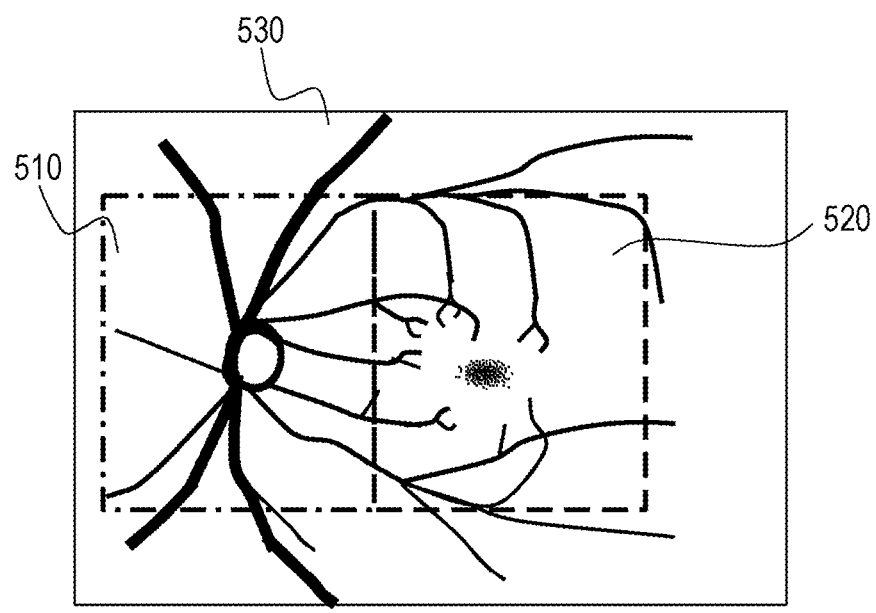
FIGS. 5A and 5B are illustrations for describing identification of a region in the image processing apparatus according to the first embodiment.
Figure 5B:
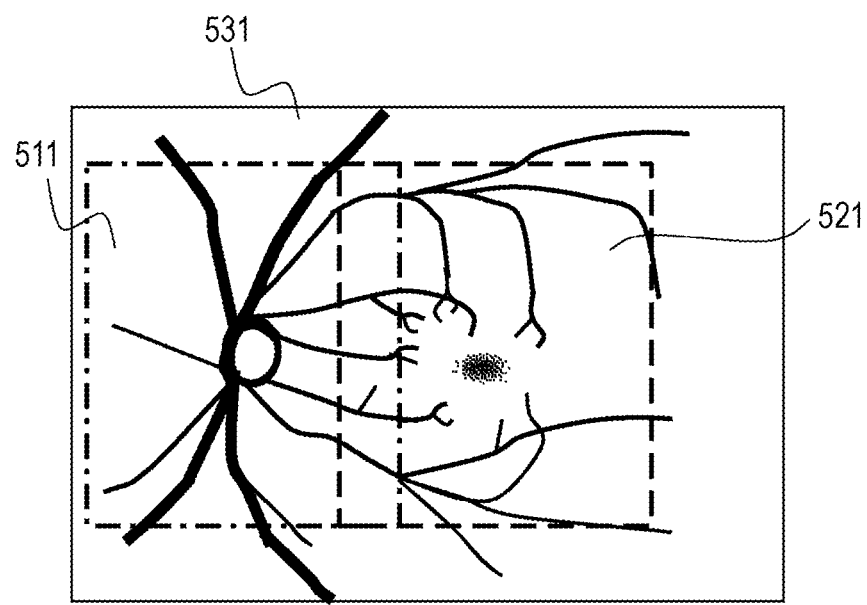

The determination portion 335 compares the features extracted by the feature extracting portion 334 with the normative database to identify a range where they exist. For example, in the case of local curvatures, the curvature values are compared to determine whether they are in the normative database. If there is a point where the curvature is outside the normative database, the place where an anomaly is present is identified by using the positions of the optic disk portion and the macula portion detected at step S207. Examples of the location where the presence of anomaly is determined may include a peripapillary region, a macula surrounding region, a wide eyeball region, both the peripapillary region and the macula surrounding region. This is described below with reference to FIGS. 5A and 5B. FIGS. 5A and 5B illustrate eye fundus images that include peripapillary regions 510 and 511, macula surrounding regions 520 and 521, and wide eyeball regions 530 and 531. FIG. 5A illustrates an example case where the regions are divided. FIG. 5B illustrates an example case where the regions partly overlap each other. One example case when the distance between the center of the optic disk portion and the fovea centralis of the macula portion is 4.0 mm is discussed below. In this case, in FIG. 5A, the position of the boundary line between the peripapillary region 510 and the macula surrounding region 520 is spaced 2.0 mm away from each of the center of the optic disk portion and the fovea centralis of the macula portion, and in FIG. 5B, the position of a boundary line between the peripapillary region 511 and the macula surrounding region 521 is spaced 3.0 mm away from the center of the optic disk portion and the position of another boundary line therebetween is spaced 3.0 mm away from the fovea centralis of the macula portion. In the case of FIG. 5B, where an overlapping region exists, when there is an anomaly area in that overlapping region, the place is identified by checking where a similar anomaly exists in other regions. For example, if the anomaly area is all contained in the region 511, it is determined that the anomaly is present in the peripapillary region. If the anomaly area is all contained in the region 521, it is determined that the anomaly is present in the macula surrounding region. If the anomaly area is in both the regions 511 and 521, it is determined that the anomaly is present in both the peripapillary region and the macula surrounding region.

In FIGS. 5A and 5B, the regions are rectangular. The shape of each of the regions is not limited to a rectangle. The region may have a circular shape or an oval shape. In FIGS. 5A and 5B, the region is displayed as being parallel to the eye fundus image. The region may be set as being parallel to a straight line that connects the center of the optic disk portion and the central section of the macula.

<Step S209: Superimposition of Region where Anomaly is Present on Eye Fundus Image>

At step S209, the display controller 305 displays an analysis result on the display portion 600. FIGS. 6A and 6B illustrate examples of a display area in the display portion 600 in the present embodiment. FIG. 6A illustrates an example normal shape. FIG. 6B illustrates an example abnormal shape. In FIGS. 6A and 6B, the reference numeral 610 indicates a tomographic image observing display area, 611 indicates a tomographic image, 612 indicates an eye fundus image, 613 indicates an imaging position and its scanning pattern mark, and 614 indicates a shape analysis graph. A region 615 surrounded by the alternate long and short dashed line in the shape analysis graph indicates a normal shape range in the retina. A display form 616 is an example of the indication whether anomaly is present in a plurality of regions in the eye fundus and shows a result of the shape analysis.

As illustrated in FIG. 6A, when the result of the shape analysis is in a normative database, the determination portion 335 displays it in the determination result 616. As illustrated in FIG. 6B, when the result of the shape analysis is outside the normative database, a region (617) where an anomaly is observed (region outside the normal shape range) is superimposed on the eye fundus image, and the location where the anomaly is observed is displayed in the determination result 616. In indicating the shape anomaly, the place where the value is not a normal value may preferably be displayed with different colors such that the shape being convex to the vitreous body side and the shape being convex to the choroid side are clearly distinguishable. For example, the shape being convex to the vitreous body side may be indicated by blue, whereas the shape being convex to the choroid side may be indicated by red. In addition, the depth of the color may vary in accordance with the magnitude of the value. Alternatively, gradations may also be used. For example, the shape being convex to the vitreous body side may be indicated using gradations from light blue to blue, and the shape being convex to the choroid side may be indicated using gradations from orange to red. If the shape anomaly is indicated by a color, a color bar 618 is provided so as to enable a user to recognize which color indicates being normal and which color indicates being abnormal.

Figure 7A:
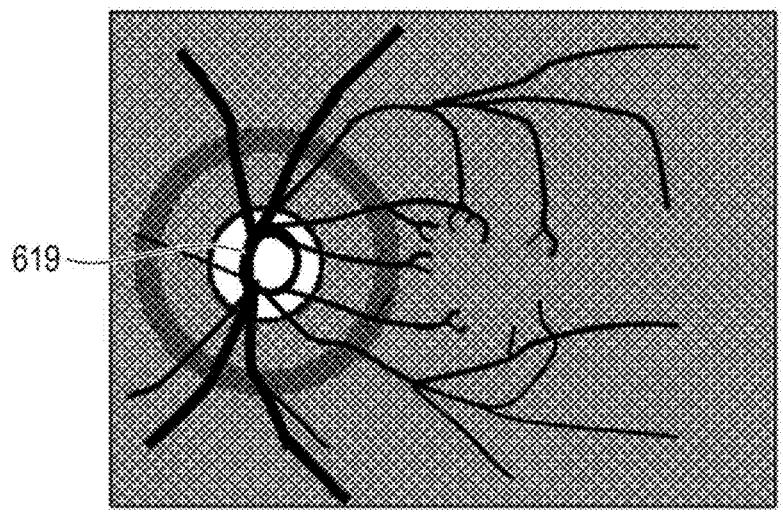
FIGS. 7A and 7B illustrate other examples of displaying analysis results on the display area in the display portion in the image processing system according to the first embodiment.
Figure 7B:
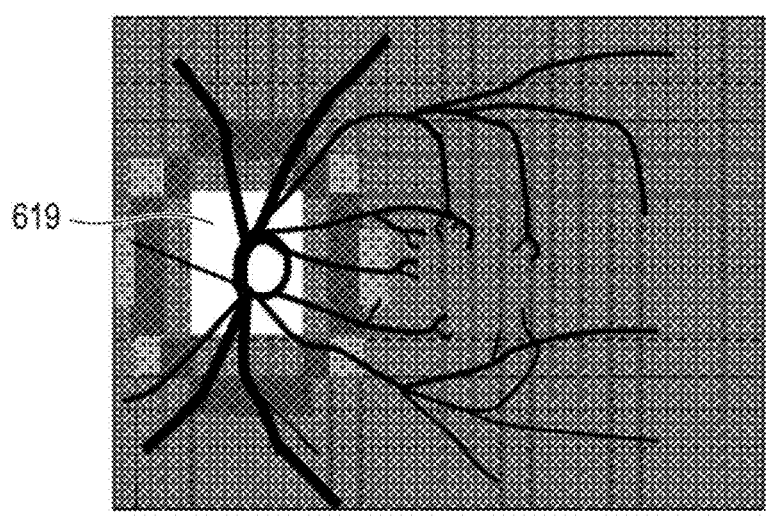

FIGS. 7A and 7B illustrate another method for displaying a result of the shape analysis. In the present embodiment, because a target layer for the shape analysis is the RPE or the Bruch's membrane, it is impossible to analyze the shape in the peripapillary region. An unanalyzable region 619 is set to avoid analyzing the shape in the peripapillary region. FIGS. 5A and 5B illustrate examples in which comparison with the normative database is conducted and areas outside the normative database are displayed. In contrast, FIGS. 7A and 7B illustrate an example in which the normative database is optional and the values obtained by the shape analysis are displayed as a color map. FIG. 7A illustrates an example in which a shape analysis result of locations corresponding to all of the imaging range is indicated on the eye fundus image 612 as a color map. For example, a normal range may be indicated by yellow or green, whereas a range outside the normal range may be indicated by blue or red. FIG. 7B illustrates an example in which the imaging range is divided into certain areas in a grid pattern and their respective mean values in the areas are indicated by colors. The present embodiment illustrates the examples with the indicating method using colors. The indicating method is not limited to these examples. When the region is divided into certain areas in a grid pattern, for example, their numerical values in the areas may be indicated by numbers. The values in the areas are not limited to the mean values. They may be maximum values, minimum values, median values, variances, or standard deviations. To evaluate characteristic values, the maximum values or minimum values may be used. To evaluate variations in the shapes of the areas, the variances or standard deviations may be used. These analytic values can be switched to any values.

<Step S210: Determination of Completion of Processing Operations>

At step S210, an instruction acquiring portion (not illustrated) acquires an instruction to end or continue capturing a tomographic image by the image processing system 100 from the outside. This instruction is input by an operator using the input portion 700. If an instruction to end processing is acquired, the image processing system 100 ends that processing. In contrast, to continue the image capturing without ending processing, the processing returns to step S202, and the image capturing continues.

In the above-described way, the image processing system 100 performs the processing.

According to the above-described configuration, retinal local shape changes can be quantitatively determined, and where and how these local shape changes are present with respect to a peripapillary portion and a macula portion can be determined. This enables retina shape image analysis, which has been mainly based on a subject, in a quantitative manner.

Second Embodiment

Determination of Type of Shape of Region where Anomaly is Present in Eye Fundus

Next, an image processing apparatus according to a second embodiment is described with reference to the drawings. The above-described first embodiment illustrates an exemplary embodiment in which a retinal shape is analyzed, the local shape is determined, and where the local shape exists is displayed. The present embodiment is characteristic in that the type of a shape of a region where an anomaly is present in an eye fundus is determined. That is, the image processing apparatus according to the present embodiment includes a determination unit configured to determine at least one type of a plurality of types (e.g., Curtin classification) corresponding to a region where an anomaly is present in an eye fundus, based on information indicating the shape of the eye fundus. The portions having substantially the same functions as in the above-described first embodiment are not described here. The image processing system 100 in the present embodiment is different in the determination portion 335, which is an example of the determination unit, and different in a determination method used in the determination portion at step S208 in the process flow in FIG. 2. This is described below with reference to FIGS. 8 and 9A to 9C.

Figure 8:
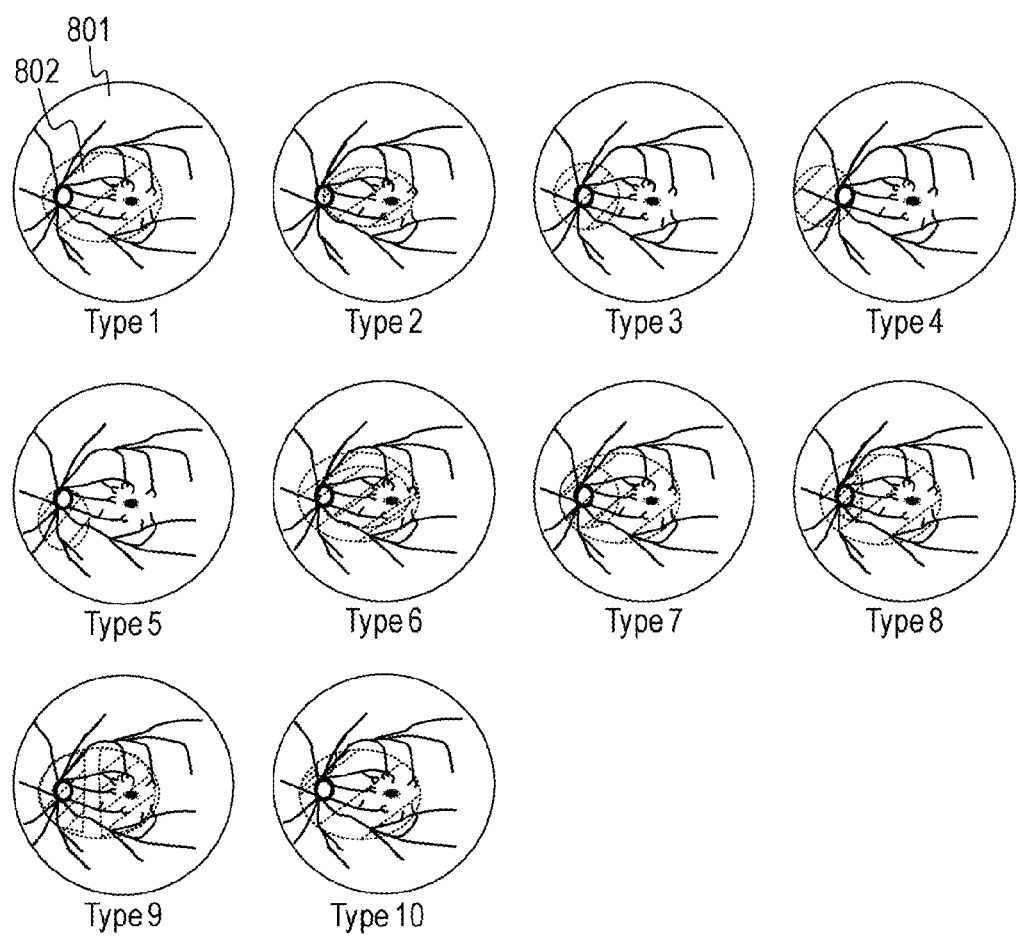
FIG. 8 includes illustrations for describing classification of morbidity of high myopia based on images captured by an eye fundus camera according to a second embodiment.

FIG. 8 illustrates 10 types classified by Curtin (examples of a plurality of types) based on images obtained by an eye fundus camera for a morbid state of high myopia. The conditions in which an ocular posterior pole degenerates and the eye axis extends (protruding region to the rear is present) in a high myopia eye are classified. In FIG. 8, the reference numeral 801 indicates an image obtained by an eye fundus camera, and 802 indicates a degenerating portion in the ocular posterior pole. Type 1 indicates posterior staphyloma, in which the degenerating portion extends from the nasal side of the optic disk portion to the macula portion, its shape is a horizontal oval, and its depth is deep. Type 2 indicates macular staphyloma, in which the degenerating portion extends from the optic disk portion to the macula portion, its shape is a horizontal oval, and its depth is shallow. Type 3 indicates peripapillary staphyloma, in which the degenerating portion extends in the peripapillary region, its shape is circular, and its depth is shallow. Type 4 indicates nasal staphyloma, in which the degenerating portion extends to the nasal side of the optic disk portion, its shape is a vertical oval, and its depth is shallow. Type 5 indicates inferior staphyloma, in which the degenerating portion extends toward the inferior side of the optic disk portion, its shape is a vertical oval, and its depth is shallow. Type 6 is combined staphyloma of type 1 and type 2. Type 7 is combined staphyloma of type 1 and type 3. Type 8 indicates tiered staphyloma, which has a tier structure. Type 9 indicates septal staphyloma, which has a septum structure. Type 10 indicates plicated staphyloma, which has a plicate structure.

Figure 9A:
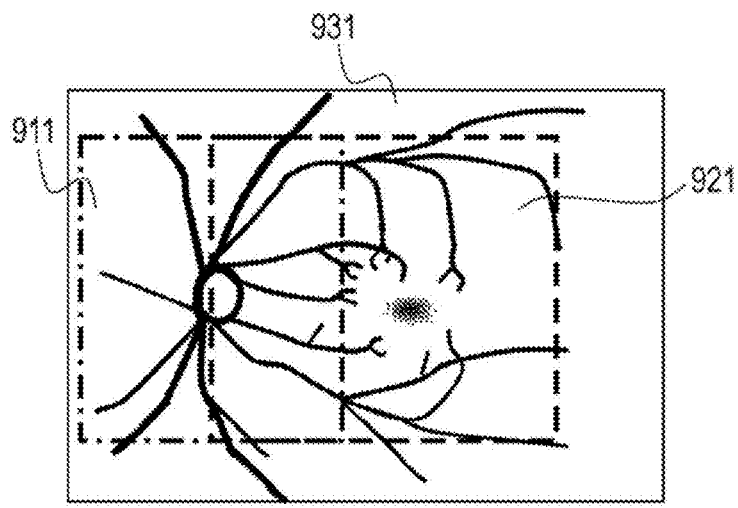
FIGS. 9A to 9C are illustrations for describing identification of a region in the image processing apparatus according to the second embodiment.
Figure 9B:
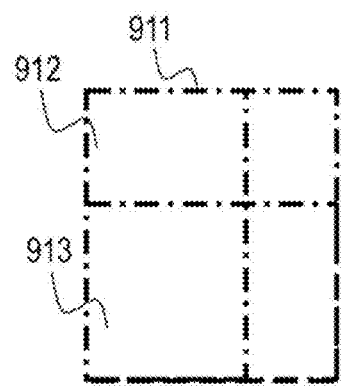
Figure 9C:
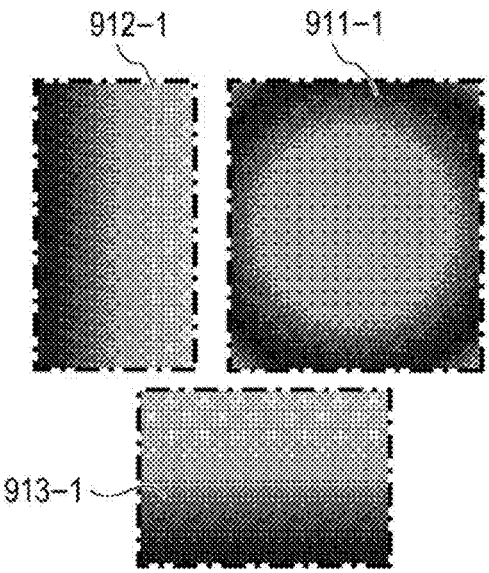

The determination portion 335 performs classification by the location of the shape change and its size. This is described below with reference to FIGS. 9A to 9C. FIG. 9A illustrates an eye fundus image in which a peripapillary region 911, a macula surrounding region 921, and a wide eyeball region 931 are depicted. FIG. 9B illustrates division of the peripapillary region 911 into a nasal region 912 of the peripapillary region and a lower region 913 of the peripapillary region. FIG. 9C illustrates example weight maps used in determination for the region of the shape change. The reference numeral 911-1 indicates a weight map for the peripapillary region. The reference numeral 912-1 indicates a weight map for the nasal region in the peripapillary region. The reference numeral 913-1 indicates a weight map for the lower region in the peripapillary region. The illustrated maps are merely examples. The weight maps are not limited to the illustrated ones, and they may be the any ones suited for classification of the types. In FIG. 9C, the weight is represented by shading. The weight in a dark location is 1, and the weight of a light location is 0.5. The weight values therebetween varies linearly. The regions 911, 912, and 913 have overlapping regions. When a change appears in only a location contained in all of the regions (e.g., lower left portion in FIG. 9B), the identification is difficult. To address this issue, by weighting a characteristic place in each region, the order of priority can be assigned in the identification. That is, the determination portion 335 checks the location where a change appears in a retina shape against the weight map, calculates the score in each region, and performs identification. The score can be calculated by using Expression 3, for example.

$$S_{Type3} = \sum_{i=0}^{n-1} \sum_{j=0}^{m-1} w_{Type3}(i, j) C(i, j) \qquad \text{Expression 3}$$

where $$C(i, j) = \begin{cases} |C(i, j)| & |C(i, j)| \geq th_c \\ 0 & \text{otherwise} \end{cases}$$

In Expression 3, $S_{type3}$ denotes the score in type 3, $W_{type3}$ denotes the weight map 911-1 in type 3, $C(i, j)$ denotes the curvature value in the peripapillary region 911, and $th_c$ denotes the threshold of the curvature value for use in calculation of the score. One example of the threshold is 0.5 [1/mm]. This corresponds to approximation by a circle of the radius 2 [mm]. The calculation using Expression 3 is performed for each region, and the score is calculated for each type. In Expression 3, the signs are neglected, and the locations having convex or concave shapes not smaller than the threshold are used in the calculation. The calculation is not limited to this method. For example, the score may be calculated by using not an absolute value but only a positive value or a negative value of the conditional expression of the curvature value. In this case, for type 3 in Curtin classification, degeneration of the ocular posterior pole is observed over the peripapillary region 911. For type 4, degeneration of the ocular posterior pole is observed in the nasal region in the peripapillary region 911 (left side in FIGS. 9A to 9C).

The determination method used by the determination portion 335 is not limited to the above-described method. For example, a classifier, such as a support vector machine (SVM), an ensemble of a classifier established by, for example, AdaBoost, or a probability model, such as a Bayesian network, may be used. In such a case, a place where a shape change is observed in a tomographic image may be projected on an eye fundus image, its x coordinate value, its y coordinate value, and the curvature value in the place where the shape change is observed may be used as the quantities of features, and the type classification may be performed by using a classifier or its ensemble. The feature extracting portion 334 may extract the quantity of features in an image, in addition to the quantity of features in a shape. For example, the classification may be performed by using the density value (shading value in RGB or black and white) in the eye fundus image or a result of an output from various types of image filters capable of enhancing a region having a high contrast of the intensity value as the quantity of features.

Next, the display area in the display portion 600 according to the present embodiment is described with reference to FIGS. 10A to 10C. In FIG. 10A, the reference numeral 1016 indicates a result of determination of the shape analysis. In FIG. 10A, a result of Curtin classification is indicated as the result of determination of the shape analysis. If the result of the shape analysis is expressed by text, some typical sentences may be prepared, and a sentence may be selected depending on the location where the shape change is observed and its size. FIG. 10B illustrates one example table used in representing the degree of the shape analysis. The degree is evaluated by referring to the table defined in advance stored in the external storage portion 500. In FIG. 10B, VALUE denotes a numerical value, and one example thereof is the score given by Expression 3. Th1 and Th2 are thresholds. The method for displaying a result is not limited to the method for displaying it by text. Another example method for displaying a result of the shape analysis is illustrated in FIG. 10C. As indicated as a shape analysis result 1016-1 in FIG. 10C, the result may be represented as a numerical value (probability). In addition to displaying only the type with the highest probability, a plurality of types with high probabilities may be displayed, thus allowing a doctor to select one.

As described above, in the present embodiment the determination unit performs classification by the shape change of a retina. This enables quantitative classification in high myopia.

The above-described embodiment is the one in which the present invention is implemented as an image processing apparatus. The embodiments of the present invention are not limited to the image processing apparatus. The present invention can be implemented as software running on a computer. A central processing unit (CPU) in the image processing apparatus controls the computer in general by using a computer program or data stored in a random-access memory (RAM) or a read-only memory (ROM). The execution of software corresponding to portions in the image processing apparatus is controlled, and the functions of the portions are achieved. A user interface, such as a button, and a display layout are not limited to those described above.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-125729, filed Jun. 18, 2014, which is hereby incorporated by reference herein in its entirety.

What is claimed is:

1. An image processing apparatus comprising:
    an image obtaining unit configured to obtain a tomographic image including a plurality of layers in an eye fundus of an eye to be examined;
    an information acquiring unit configured to acquire information indicating a shape of a macula portion and an optic disk portion in at least one layer in the tomographic image; and
    a determination unit configured to determine whether an anomaly is present in the macula portion and the optic disk portion based on the information indicating the shape.

2. The image processing apparatus according to claim 1, wherein
    the determination unit is configured to determine whether the anomaly is present in the macula portion and the optic disk portion by comparing the information indicating the shape with a normative database storing shapes of normal eye fundi.

3. The image processing apparatus according to claim 1, further comprising:
    a region detecting unit configured to detect at least one of the optic disk portion and the macula portion based on at least one of the tomographic image and an eye fundus image of the eye to be examined,
    wherein the determination unit is configured to determine whether the anomaly is present in the detected optic disk portion and macula portion based on the information indicating the shape and to determine a type of a disease in the eye fundus based on the determination.

4. The image processing apparatus according to claim 1, further comprising:
a display control unit configured to display a region where the presence of the anomaly is determined on a display unit such that the region is superimposed on an eye fundus image of the eye to be examined.

5. The image processing apparatus according to claim 4, wherein
the display control unit is configured to display a display form indicating whether the anomaly is present in the macula portion and the optic disk portion on the display unit.

6. The image processing apparatus according to claim 4, wherein the display control unit is configured to display the information indicating the shape on the display unit.

7. The image processing apparatus according to claim 1, wherein
the determination unit is configured to determine a type of a disease in the eye fundus, the disease corresponding to a region where the presence of the anomaly is determined.

8. The image processing apparatus according to claim 1, wherein
the determination unit is configured to determine a state of the anomaly, in a region where the presence of the anomaly is determined, based on the information indicating the shape and to determine a type of a disease in the eye fundus, the disease corresponding to the region where the presence of the anomaly is determined and corresponding to the state of the anomaly.

9. The image processing apparatus according to claim 1, wherein
the information acquiring unit is configured to acquire at least one of a value of a curvature in the layer in the tomographic image and a value indicating a region from the layer to a reference line, as the information indicating the shape, and
the determination unit is configured to determine whether the anomaly is present in the macula portion and the optic disk portion by comparing the acquired value with a threshold.

10. The image processing apparatus according to claim 1, further comprising:
a layer detecting unit configured to detect at least one of a Bruch layer and a retinal pigment epithelium (RPE) layer from the tomographic image,
wherein the information acquiring unit is configured to acquire the information indicating the shape based on the detected layer.

11. The image processing apparatus according to claim 1, wherein
the image processing apparatus is connected to a tomographic imaging apparatus so as to be able to communicate therewith, and
the image obtaining unit is configured to obtain the tomographic image obtained by the tomographic imaging apparatus capturing an image of the eye fundus.

12. The image processing apparatus according to claim 11, wherein
the tomographic imaging apparatus includes a selection unit configured to select any one of a plurality of imaging modes including a shape analysis imaging mode being an imaging mode at which the shape of the eye fundus is analyzed, and the image obtaining unit is configured to obtain the tomographic image, the tomographic image being obtained by the tomographic imaging apparatus capturing the image and including the optic disk portion and the macula portion in the eye fundus, when the shape analysis imaging mode is selected.

13. An image processing method comprising:
a step of obtaining a tomographic image including a plurality of layers in an eye fundus of an eye to be examined;
a step of acquiring information indicating a shape of a macula portion and an optic disk portion in at least one layer in the tomographic image; and
a step of determining whether an anomaly is present in the macula portion and the optic disk portion based on the information indicating the shape.

14. The image processing method according to claim 13, wherein
in the determining step, a type of a disease in the eye fundus, the disease corresponding to a region where the presence of the anomaly is determined.

15. The image processing method according to claim 13, wherein
in the determining step, a state of the anomaly in a region where the presence of the anomaly is determined is determined based on the information indicating the shape, and a type of a disease in the eye fundus is determined, the disease corresponding to the region where the presence of the anomaly is determined and corresponding to the state of the anomaly.

16. The image processing method according to claim 13, wherein
in the step of acquiring the information, at least one of a value of a curvature in the layer in the tomographic image and a value indicating a region from the layer to a reference line, as the information indicating the shape, and
in the determining step, it is determined whether the anomaly is present in the macula portion and the optic disk portion by comparing the acquired value with a threshold.

17. A storage medium enabling execution of the image processing method according to claim 13.

18. An image processing apparatus comprising:
an image obtaining unit configured to obtain a tomographic image including a plurality of layers in an eye fundus of an eye to be examined;
an information acquiring unit configured to acquire information indicating a shape of at least one layer in the tomographic image; and
a determination unit configured to determine at least one type of a plurality of types corresponding to a region where an anomaly is present in the eye fundus.

19. An image processing method comprising:
a step of obtaining a tomographic image including a plurality of layers in an eye fundus of an eye to be examined;
a step of acquiring information indicating a shape of at least one layer in the tomographic image; and
a step of determining at least one type of a plurality of types corresponding to a region where an anomaly is present in the eye fundus.

20. A storage medium enabling execution of the image processing method according to claim 19.

* * * * *